United States Patent
Drohan et al.

(10) Patent No.: US 9,587,008 B2
(45) Date of Patent: Mar. 7, 2017

(54) METHOD OF PRODUCING RECOMBINANT VITAMIN K DEPENDENT PROTEINS

(71) Applicant: APTEVO BIOTHERAPEUTICS LLC, Seattle, WA (US)

(72) Inventors: William N. Drohan, Springfiled, VA (US); Michael J. Griffith, San Juan Capistrano, CA (US)

(73) Assignee: APTEVO BIOTHERAPEUTICS LLC, Seattle, WA (US)

( * ) Notice: Subject to any disclaimer, the term of this patent is extended or adjusted under 35 U.S.C. 154(b) by 0 days.

(21) Appl. No.: 14/475,881

(22) Filed: Sep. 3, 2014

(65) Prior Publication Data
US 2014/0369994 A1    Dec. 18, 2014

Related U.S. Application Data

(63) Continuation of application No. 13/459,743, filed on Apr. 30, 2012, now abandoned, which is a continuation of application No. PCT/US2010/054581, filed on Oct. 28, 2010.

(60) Provisional application No. 61/256,802, filed on Oct. 30, 2009.

(51) Int. Cl.
*C12P 21/02*    (2006.01)
*C07K 14/745*   (2006.01)
*A61K 38/36*    (2006.01)
*C12N 9/50*     (2006.01)

(52) U.S. Cl.
CPC ............ *C07K 14/745* (2013.01); *A61K 38/36* (2013.01); *C12N 9/50* (2013.01); *C12P 21/02* (2013.01)

(58) Field of Classification Search
None
See application file for complete search history.

(56) References Cited

U.S. PATENT DOCUMENTS

| | | |
|---|---|---|
| 4,784,950 A | 11/1988 | Hagen et al. |
| 2007/0122884 A1 | 5/2007 | Pingel et al. |
| 2008/0045453 A1 | 2/2008 | Drohan et al. |
| 2012/0276079 A1 | 11/2012 | Drohan et al. |

FOREIGN PATENT DOCUMENTS

| | | | |
|---|---|---|---|
| JP | H07-163375 A | 6/1995 | |
| WO | WO 98/49289 A1 | 11/1998 | |
| WO | WO 2008/022151 A1 * | 2/2008 | ............. A61K 38/36 |

OTHER PUBLICATIONS

International Search Report, PCT appl. No. PCT/US2010/054581, 2 pages (mailed Dec. 17, 2010).
Supplemental European Search Report, EP appl. No. 10827499.4, 8 pages (May 13, 2013).
Sutkeviciute et al., The influence of different glycosylation patterns on factor VII biological activity,: Biochemie 91(9):1123-1130 (2009).
Van Staveren et al., "Light scattering in Intralipid-10% in the wavelength range of 400-1100 nm," Appl. Optics 30(31):4507-4514 (1991).
European Patent Application No. 10827499.4, Office Action mailed Aug. 26, 2016, 4 pages.

* cited by examiner

*Primary Examiner* — Jim Ketter
(74) *Attorney, Agent, or Firm* — Cooley LLP

(57) ABSTRACT

Methods for producing cell lines with high levels of biologically active recombinant vitamin K dependent proteins are described. The transfected cell lines do not include heterologous genes for processing enzymes and are not subject to selection pressure such as methotrexate resistance. Cell lines producing Factor VII/VIIa and Factor IX are described. These cell lines can be used for isolation of Factor VII/VIIa and/or Factor IX for treatment of Hemophilia.

14 Claims, 2 Drawing Sheets

METHOD OF PRODUCING RECOMBINANT VITAMIN K DEPENDENT PROTEINS

RELATED APPLICATIONS

This application is a continuation of U.S. application Ser. No. 13/459,743, filed Apr. 30, 2012, which is a continuation of International Application No. PCT/US2010/054581, filed Oct. 28, 2010, which claims priority to U.S. Provisional Application No. 61/256,802, filed Oct. 30, 2009, the contents of all of which are incorporated by reference in their entireties.

BACKGROUND OF THE INVENTION

Field of the Invention

The invention related to recombinant vitamin K dependent proteins and methods of preparing the protein in a mammalian cell without the use of heterologous post-translational modification enzymes.

Description of the Related Art

Bleeding disorders can result from a deficiency in the functional levels of one or more of the blood proteins, collectively known as blood coagulation factors, that are required for normal hemostasis, i.e. blood coagulation. The severity of a given bleeding disorder is dependent on the blood level of functional coagulation factors. Mild bleeding disorders are generally observed when the functional level of a given coagulation factor reaches about 5% of normal, but if the functional level falls below 1%, severe bleeding is likely to occur with any injury to the vasculature.

Medical experience has shown that essentially normal hemostasis can be temporarily restored by intravenous infusion of biological preparations containing one or more of the blood coagulation factors. So-called replacement therapy, whereby a biological preparation containing the deficient blood coagulation factor is infused when bleeding occurs (on demand) or to prevent bleeding (prophylactically), has been shown to be effective in managing patients with a wide variety of bleeding disorders. In general, for replacement therapy to be effective, intravenous infusions of the missing coagulation factor are targeted to achieve levels that are well above 5% of normal over a two- to three-day period.

Historically, patients who suffer from hemophilia, a genetically acquired bleeding disorder that results from a deficiency in either blood coagulation Factor VIII (hemophilia A) or Factor IX (hemophilia B), were successfully treated by periodic infusion of whole blood or blood plasma fractions of varying degrees of purity.

More recently, with the advent of biotechnology, biologically active preparations of synthetic (recombinant) blood coagulation factors have become commercially available for treatment of blood coagulation disorders. Recombinant blood coagulation proteins are essentially free of the risks of human pathogen contamination that continue to be a concern that is associated with even high purity commercial preparations that are derived from human blood.

Several of the proteins required for normal blood coagulation are very complex in terms of having multiple structural domains each being associated with a very specific functional property that is essential for the overall effectiveness of the protein in controlling hemostasis and/or preventing thrombosis. In particular, the so-called "vitamin K-dependent" blood coagulation proteins, e.g. Factors II, VII, IX, X, Protein C and Protein S, are very complex proteins and must undergo extensive post-translational modification for normal function. Achieving high levels of functional vitamin K-dependent proteins by recombinant technology has been limited by the structural complexity of these proteins and the inability to create genetically engineered cell systems that overcome the inherent deficiencies in the enzymatic activities required for efficient and complete post-translational modification to occur.

Kaufman, et al, (Kaufman, et al. (1986) The Journal of Biological Chemistry, vol. 261 no, 21: 9622-9628) report the production of recombinant, biologically active Factor IX. However, while upwards of 100 µg/mL of Factor IX was produced, the level of active material was only 1.5%.

Other vitamin K dependent proteins have been produced recombinantly with limited success. Jorgensen, et al. (Jorgensen, et al. (1987) The Journal of Biological Chemistry, vol. 262-(14): 6729-6734) report that human prothrombin was produced in CHO cells at a level of up to 0.55 µg/ml. At this level, the prothrombin was all biologically active. However, when levels were increased 10-15 fold, biological activity dropped to 60%. They hypothesized that the γ-carboxylation system of CHO cells is limited and that only a certain level of protein can be efficiently processed.

Messier, et al. (Messier, et al. (1991) Gene vol. 99: 291-294) cloned and expressed human Factor X in COS-1 Monkey kidney Cells. Both the level produced (0.25-0.27 µg/ml) and the biological activity (9-10%) were low.

Herlitschka, et al. (Herlitschka, et al, (1996) Protein Expression and Purification vol. 8: 358-364) used human prothrombin as a reporter with hygromycin phosphotransferase/dihyrofolate reductase (DHFR) as a dominant selection/amplification fusion marker. Levels of up to 200-250 mU/$10^6$ cells/24 hours were produced using 293 kidney cells and 5-15 mU/$10^6$ cells/24 hours using CHO cells. Taking 1 Unit as equivalent to about 100 µg, this translates to a maximum level of 25 µg using 293 cells. Although the relative biological activity was not determined, the authors indicated that the 293 cells had been chosen because of its high carboxylation potential.

Himmelspach, et al. (Himmelspach, et al. (2000) Thrombosis Research vol. 97:51-67) obtained 120 µg/mL/day of recombinant human Factor X using DHFR deficient CHO cells with methotrexate selection. Biological activity was up to 25%. The role of Furin in processing of Factor X was investigated by these workers. While Factor X, like Factor IX, also requires gamma carboxylation and post-translational cleavage, it is not clear why higher levels of Factor X having biological activity have been obtained compared to Factor IX. Significant amounts of the recombinant Factor X produced remained covalently attached to the propeptide and/or remained as a single chain precursor. In the presence of recombinant Furin (PACE), the amount of biologically active Factor X approximately doubled (from 22% to 43%). In Factor X, removal of the propeptide appeared to rely upon an endopeptidase other than Furin, while light/heavy chain processing was furin-dependent.

Sun, et al. (Sun, et al. (2005) Blood vol, 106 (12): 3811-3815) reported tht the percentage of carboxylated Factor X can be increased from 50% to 95% by coexpression of Vitamin K epoxide reductase (VKOR).

Wasley, et al. (Wasley, et al. The Journal of Biological Chemistry vol. 268 (12): 8458-8465, 1993) reported that Factor IX is poorly processed in Chinese Hamster Ovary (CHO) cells but that coexpression of PACE (Paired basic Amino acid Cleaving Enzyme) improved processing and specific activity 2-3 fold.

Among the problems encountered in recombinant systems is that in order to produce biologically active Factor IX and Factor VII/VIIa, substantial gamma-carboxylation of glutamic acid residues in the amino terminal region of the protein referred to as the gla-domain, is needed. For example, FVII/VIIa has 10 gla residue sites which should be carboxylated and Factor IX has 12. A majority of these residues must be gamma-carboxylated in order to have bioaetive protein. Additionally, pro-Factor IX, a form of Factor IX that contains a propeptide domain that is required for the efficient intracellular gamma-carboxylation of the protein, must be processed properly prior to secretion, as must Factor VII be processed prior to secretion.

One approach is to co-transfect with genes encoding enzymes which function to post-translationally process Factor IX. Appropriate enzymes include Vitamin K dependent γ-glutamyl carboxylase (VKGC), Vitamin K dependent epoxide reductase (VKOR), and Paired basic amino acid converting enzyme (PACE). U.S. application Ser. No. 11/643,563, filed Dec. 21, 2006 is directed to this approach.

VKGC incorporates a carboxyl group into glutamic acid to modify multiple residues within the vitamin K dependent protein within about 40 residues of the propeptide, within the so-called "gla domain", VKOR is important for vitamin K dependent proteins because vitamin K is converted to vitamin K epoxide during reactions in which it is a cofactor. The amount of vitamin K in the human diet is limited. Therefore, vitamin K epoxide must be converted back to vitamin K by VKOR to prevent depletion. Consequently, co-transfection with VKOR enhances the appropriate cycling of vitamin K inside the cell and provides sufficient vitamin K for proper functioning of the vitamin K dependent enzymes such as VKGC. The term "PACE" is an acronym for paired basic amino acid converting (or cleaving) enzyme; PACE, is a subtilisin-like endopeptidase, i.e., a propeptide-cleaving enzyme which exhibits specificity for cleavage at basic, residues of a polypeptide, e.g., -Lys-Arg-, -Arg-Arg, or -Lys-Lys-.

While the above mentioned enzymes may be incorporated into a transgenic cell line for processing of vitamin K dependent proteins, mammalian cells naturally produce certain levels of these enzymes endogenously.

The approach taken here is a process of initial selection, whereby a gene, such as a DNA sequence with introns or a cDNA encoding a gene product for a vitamin K dependent protein such as Factor VII or Factor IX is cloned into mammalian cells, followed by selection for transfected clones. The high level expressers are identified, isolated and optionally pooled and may be re-cloned. In any case, the cloned cells are cultured to select even higher expressing clones. The method selects for cell lines which express high levels of vitamin K dependent proteins without requiring co-transfection with multiple heterologous genes, such as genes encoding enzymes necessary for the post-translational modification of vitamin K dependent proteins.

DEFINITIONS

The term cloning as used herein refers to manipulations for isolating and establishing clones. The term "clone" has its usual and customary meaning and refers to a population of cells produced generated from a single parent cell and which therefore should be genetically identical. In some embodiments, limit dilution cloning is used to produce high producing clones. "Limit dilution cloning" has its usual and customary meaning and refers to a process of obtaining a monoclonal cell population starting from a polyclonal mass population of cells. The starting (polyclonal) culture is serially diluted until a single cell is statistically isolated and used to derive a monoclonal culture is obtained.

In alternate embodiments, "semi-solid matrix cloning" methods are used. Semi-solid matrix cloning refers to seeding cells at very low densities into a semi-solid matrix, typically although not necessarily following a the transfection and selection process. Preferably, the cells are seeded into a semi-solid matrix with as few population doublings as possible. The shortest number of population doublings minimizes the risk of losing the highest expressing cells in the original mixed population, since these cells would carry the greatest metabolic burden and likely be overgrown by the faster growing cells that express lower levels of recombinant protein or none at all.

Cells are seeded at very low densities (typically 1,000-4,000 but may be as high as 10,000 cells per ml) into a mixture of media, media supplements, conditioned medium (usually 5-20% volume:volume), and a generally inert, biologically compatible, semi-solid medium such as methylcellulose. After seeding the low density cells into the mixture as a low density single cell suspension and letting it "gel" for a few minutes into a semi-solid, the culture plates are returned to an incubator (37° C., with humidity and carbon dioxide buffering atmosphere) and allowed to sit undisturbed for anywhere from ~1 week to ~3 weeks. During this time many of the suspended single cells will grow slowly but eventually begin to replicate and form "colonies" representing a cluster of daughter cells all genetically identical to the single suspended cell from which they were derived. About two weeks after initially seeding the cells into the semisolid matrix one observes the culture plates for colony formation (number of colonies, their size and how far separated they are from one another in the gel) and then individual colonies are picked and seeded into separate cluster plates, each as a clonal population. They are expanded thru larger plates and screened.

The term "bioactive" as used herein in reference to vitamin K dependent proteins is a broad term which has its usual and customary meaning of a substance which has an effect on living matter. In the present context the meaning is expanded to include zymogen forms which may not be bioactive per se but are capable of activation. Activation may be by administration to a living body (that is, activation occurs within the body after administration by endogenous factors) or may be in vitro activated by treatment with an appropriate enzyme or set of incubation conditions (e.g. pH, concentration, temperature, etc.). For example, in the case of Factor VII, proteolytic cleavage is needed to convert the zymogen, Factor VII, to the active form Factor VIIa. Likewise, Factor IX is a zymogen which requires proteolytic cleavage to Factor IXa. In the context of the invention, Factor VIIa and Factor IXa are considered "bioactive". However, Factor VII and Factor IX are also considered to be "bioactive" if they have been appropriately post-translationally modified, (with Gla residues for example), so that they are capable of being converted to the bioactive form either in vivo or in vitro.

The term "gene" as used herein has its usual and customary meaning of a DNA sequence which may contain introns and exons and also includes a cDNA encoding a gene product.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy.

Furthermore, treatment may include acts that may worsen the patient's overall feeling of well-being or appearance.

SUMMARY OF THE INVENTION

Embodiments of the invention are directed to cell lines which produce recombinant vitamin K dependent protein having at least 20% biological activity. Preferably, the cell line does not contain heterologous genetic material encoding proteins involved in the post-translation modification of vitamin K dependent proteins. Preferably, the cell line is a mammalian cell line, more preferably, the mammalian cell line is a Chinese Hamster Ovary (CHO) cell line. Preferably, the gene encoding the Vitamin K dependent protein is operably linked to the Chinese hamster elongation factor 1 (CHEF-1) promoter.

In some embodiments, the cell line is cultured in a media that includes vitamin K. In some embodiments, the cell line is cultured in a media that does not include vitamin K.

In some embodiments, the cell line does not contain heterologous DHFR. In preferred embodiments, the cell line has not been subjected to selection with methotrexate.

Preferably, Vitamin K dependent protein is Factor II, Factor VII, Factor IX, Factor X, Protein C or Protein S, and more preferably, Factor VII/VIIa or Factor IX.

Embodiments of the invention are directed to methods of producing a recombinant biologically active Vitamin K dependent protein which include one or more of the following steps:
(a) transfecting a population of mammalian cells with a gene encoding the Vitamin K dependent protein operably linked to a promoter;
(b) performing at least one round of cloning and screening to identify cell clones which produce at least 10 mg/L of the Vitamin K dependent protein which is at least 10% biologically active;
(c) optionally, repeating the cell cloning of step (b) one or more times to identify single cells producing more than 10 mg/L of the Vitamin K dependent protein which is at least 10% biologically active; and
(d) harvesting the Vitamin K dependent protein.

Preferably, the Vitamin K dependent protein of the method is Factor II, Factor VII, Factor IX, Factor X, Protein C or Protein S, more preferably Factor IX or Factor VII. In preferred embodiments, the Vitamin K dependent protein is operably linked to the Chinese hamster elongation factor 1 (CHEF-1) promoter. In preferred embodiments, the mammalian cell line is a Chinese Hamster Ovary Cell line. The media may optionally include Vitamin K.

Preferably, cloning is by limit dilution cloning or semi-solid matrix cloning methods. More preferably, limit dilution cloning is used for producing recombinant Factor IX and semi-solid matrix cloning is used for producing recombinant Factor VII/VIIa.

In preferred embodiments, the method may include pre-selecting cells producing at leak 10 mg/L Vitamin K dependent protein antigen, preferably Factor VII/VIIa or Factor IX antigen, before step (b). In some embodiments, cells are selected which produce at least 10 mg/L Vitamin K dependent protein antigen, preferably Factor VII/VIIa or Factor IX antigen, after step (b).

In preferred embodiments, the Vitamin K dependent protein is Factor IX and at least 20%, more preferably at least 30%, and yet more preferably at least 40% of the Vitamin K dependent protein is biologically active. In a most preferred embodiment, at least 58% of the Vitamin K dependent protein is biologically active.

In preferred embodiments, the Vitamin K dependent protein is Factor VII/VIIa and at least 60%, more preferably 70%, more preferably 80%, more preferably 90%, more preferably 95%, more preferably 98%, more preferably 99% and most preferably 100% of the Vitamin K dependent protein is biologically active.

In preferred embodiments, the vitamin K dependent protein is produced in an amount of at least 20 mg/L, more preferably at least 30 mg/L, and yet more preferably at least 40 mg/L.

Embodiments of the invention are directed to recombinant Vitamin K dependent proteins and pharmaceutical preparations containing Vitamin K dependent proteins, in particular Factor VII/VIIa protein and Factor IX protein, where the protein is produced by any of the methods described above.

Embodiments of the invention also include kits which may include one or more Vitamin K dependent proteins, preferably as a pharmaceutical composition. Preferably the kit includes Factor VII/VIIa or Factor IX protein in a pharmaceutically acceptable carrier.

Embodiments of the invention are directed to methods of treating hemophilia by administering an effective amount of a pharmaceutical preparation of a Vitamin K dependent protein, in particular where the Vitamin K dependent protein is Factor VII/VIIa or Factor IX, to a patient in need of treatment for hemophilia or uncontrollable hemorrhage.

Embodiments of the invention are directed to recombinant Factor. IX proteins having at least 10%, more preferably 20%, yet more preferably 30%, yet more preferably 40% and yet more preferably 58% biological activity.

Embodiments of the invention are directed to Factor VII/VIIa protein having at least 60%, more preferably 70%, more preferably 80%, more preferably 90%, more preferably 95%, more preferably 98%, more preferably 99% and most preferably 100% biological activity.

Embodiments of the invention are directed to cell lines which produce recombinant vitamin K dependent protein having at least 20% biological activity. Preferably, the cell line is generated by transfecting a population of mammalian cells with a cDNA encoding the Vitamin K dependent protein operably linked to a Chinese hamster elongation factor 1 (CHEF-1) promoter; and performing at least one round of cloning and screening to identify cell clones which produce at least 10 mg/L of the Vitamin K dependent protein which is at least 10% biologically active. Preferably, techniques of limit dilution cloning or semi-solid matrix cloning are used.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

DETAILED DESCRIPTION OF THE PREFERRED EMBODIMENT

Figure 1:
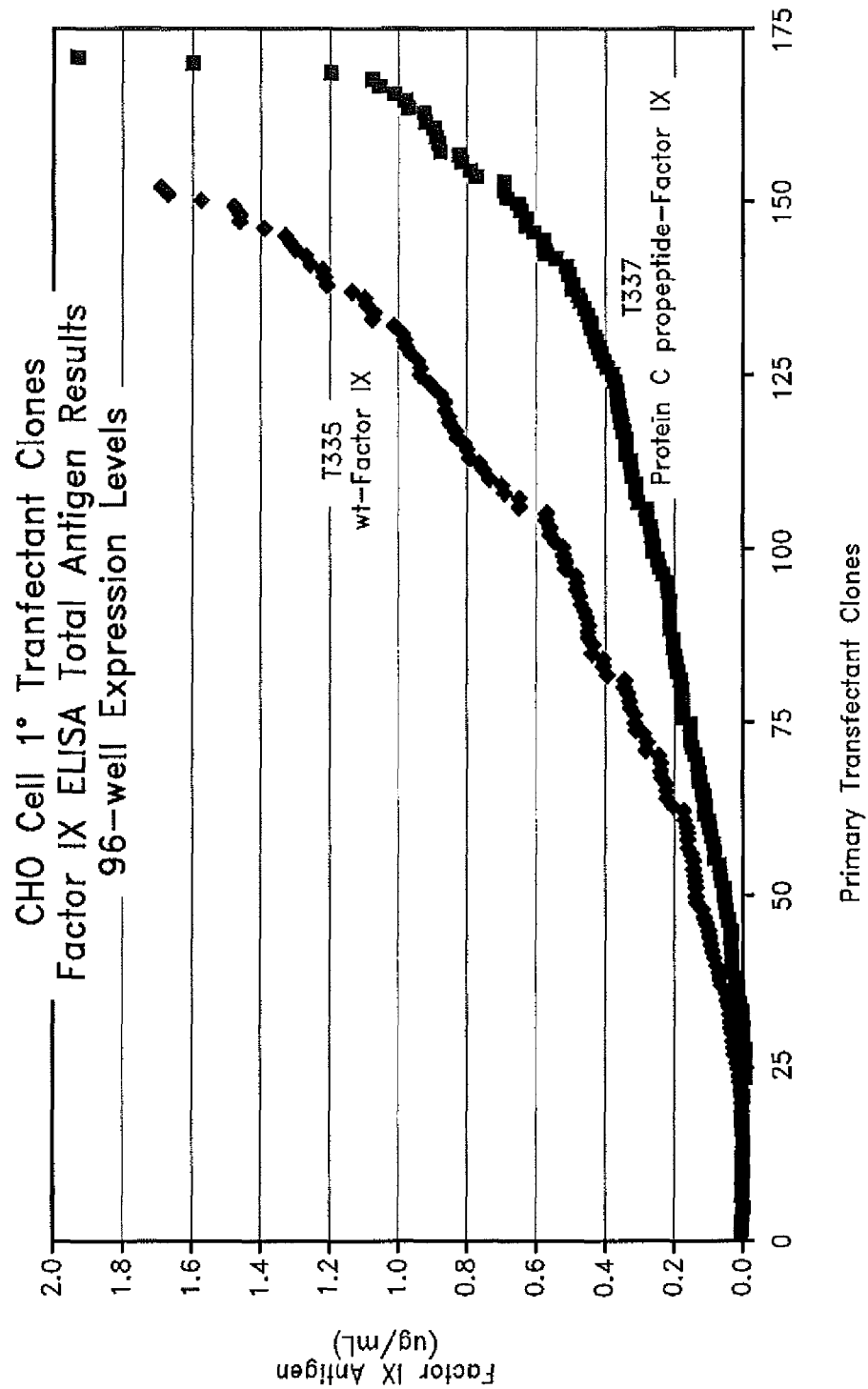
FIG. 1 shows Factor IX ELISA total antigen results for CHO cell first transfectant clones. There were 152 T335 clones and 171 T337 clones.

Kaufman, et al. (supra) teach a method of increasing the expression level of a gene encoding Factor IX in CHO cells by including a gene encoding DHFR on the plasmid containing the gene for Factor IX and using the selective pressure of increasing levels of methotrexate. As the cells having a high copy number of the plasmid encoding DHFR are selected by increasing methotrexate levels, increased levels of Factor IX are also produced. However, the limitation of this method is that, while reasonably high levels of Factor IX are produced, the level of the processing-enzymes remain low. So most of the Factor IX produced by this method is not biologically active.

While one approach to address this problem is to add heterologous processing enzymes, processing of Vitamin K dependent proteins is complex. Other factors may be involved which then become limiting in the presence of heterologous factors.

In contrast, the present selection method selects for cell lines which produce high levels of biologically active vitamin K dependent proteins. The nucleic acid encoding the vitamin K dependent protein of interest is cloned into a vector where it is operably linked to a strong promoter, preferably CHEF-1. This approach does not rely upon methotrexate selection and selects for optimal levels of all of the necessary post-translational enzymes, as well as vitamin K dependent protein. Vitamin K dependent proteins include Factors II, VII, IX, X, Protein C and Protein S. In particular, the present inventors have found that for production of both recombinant Factor VII/VIIa and Factor IX protein, use of the CHEF-1 promoter operably linked to a gene coding for Factor VII/VIIa or Factor IX in the present method produces very high levels of biologically active Factor VII/VIIa or Factor IX, even without introduction of genes for processing factors and/or addition of processing factors to provide means for post-translational processing of the recombinant Factor VII/VIIa and Factor IX proteins.

Any appropriate cell line may be used including, but not limited to insect cells, plant cells and mammalian cells. Mammalian cell lines include Chinese Hamster Ovary (CHO) cells and HEK 293 cells. The cell may be selected from a variety of sources, but is otherwise a cell that may be transfected with an expression vector containing a nucleic acid, preferably a cDNA of a vitamin K-dependent protein.

In some embodiments, from a pool of transfected cells, clones are selected that produce quantities of the vitamin K-dependent protein over a range (Target Range) that extends from the highest level to the lowest level that is minimally acceptable for the production of a commercial product. Cell clones that produce quantities of the vitamin K-dependent protein within the Target Range may be combined to obtain a single pool or multiple sub-pools that divide the clones into populations of clones that produce high, medium or low levels of the vitamin K-dependent protein within the Target Range. Alternatively, the clones are not pooled but are maintained as monoclonal cultures. It is considered to be within the scope of the present invention that transfected cells that produce a vitamin K-dependent protein within the Target Range may be analyzed to determine the extent to which fully functional protein is produced. Levels of vitamin K dependent protein antigen may be determined by conventional ELISA. Commercial kits are available such as VisuLize® (Factor IX Antigen ELISA kit from Affinity biologicals (Aneaster, Ontario, Canada).

In preferred embodiments of the method of the present invention, the selected transfectant pool is cloned to determine the optimal level of production of fully functional vitamin K-dependent protein. It is contemplated that higher percentages of fully functional vitamin K-dependent protein will be produced by cell clones that produce lower total amounts of the vitamin K-dependent protein within the Target Range. In preferred embodiments, the optimal level of production will be the highest level of functional vitamin K-dependent protein.

Means to assay bioactivity of vitamin K dependent proteins are well known and include one- and two-stage clotting assays as well as chromogenic assays. For example, assay of Factor IX may use a Universal Coagulation Reference Plasma (UCRP) as a standard for Factor IX activity and Factor IX-deficient plasma for dilution of calibration standards and unknown samples. The assay involves mixing plasma with activator and calcium chloride to initiate the clotting cascade, with formation of the fibrin clot measured by absorbance. The clotting time measured in this assay is the aPTT (activated partial thromboplastin time), the time required for the absorbance to cross a pre-determined threshold value. Accurate determination of Factor IX activity is achieved by comparing the signal of the unknowns to Factor IX Reference Standard (UCRP) assayed simultaneously. In preferred embodiments, the assay is conducted on an automated coagulation analyzer. Potency in units/mL is obtained by use of an international WHO standard for blood coagulation factor IX.

Clotting assays are also known for FVII/FVIIa (U.S. Pat. No. 5,750,358 which is incorporated herein by reference).

Chromogenic assays include conventional chromogenic FVIIa Bioactivity assays such as BIOPHEN FVII® (Ref No. 221304) available from HYPHEN BioMed. A cleavage product produced during the assay is measured spectrophotometrically.

Genetic Engineering Techniques

The practice of the present invention employs, unless otherwise indicated, conventional techniques of molecular biology, microbiology, recombinant DNA, and immunology, which are within the skill of the art. Such techniques are explained fully in the literature. See, e.g., Sambrook, et al., "Molecular Cloning; A Laboratory Manual", 2nd ed (1989); "DNA Cloning", Vols. I and II (D. N Glover ed. 1985); "Oligomicleotide Synthesis" (M. J. Gait ed. 1984); "Nucleic Acid Hybridization" (B. D. Hames & S. J. Higgins eds. 1984); "Transcription and Translation" (B, D. Hames & S. J. Higgins eds. 1984); "Animal Cell Culture" (R. I. Freshney ed. 1986); "Immobilized Cells and Enzymes" (IRL Press, 1986); B. Perbal, "A Practical Guide to Molecular Cloning" (1984); the series, Methods in Enzymology (Academic Press, Inc.), particularly Vols. 154 and 155 (Wu and Grossman, and Wu, eds., respectively); "Gene Transfer Vectors for Mammalian Cells" (J. H. Miller and M. P. Calos eds. 1987, Cold Spring Harbor Laboratory); "Immunochemical Methods in Cell and Molecular Biology", Mayer and Walker, eds. (Academic Press, London, 1987); Scopes, "Protein Purification: Principles and Practice", 2nd ed. 1987 (Springer-Verlag, N.Y.); and "Handbook of Experimental Immunology" Vols I-IV (D. M. Weir and C. C. Blackwell eds 1986). All patents, patent applications, and publications cited in the background and specification are incorporated herein by reference.

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col, 14 line 12; and U.S. Pat. No. 4,879,224 to Wallner at Col. 6 line 8 to Col. 8 line 59.

Expression Vectors

A vector is a replicable DNA construct. Many transfection methods to create genetically engineered cells that express large quantities of recombinant proteins are well known. Embodiments of the invention are not dependent on the use of any specific expression vector. In preferred embodiments, cells are transfected with an expression vector that contains the cDNA encoding the protein.

Vectors are used herein either to amplify DNA encoding Vitamin K Dependent Proteins and/or to express DNA which encodes Vitamin K Dependent Proteins. An expression vector is a replicable DNA construct in which a DNA sequence encoding a Vitamin K dependent protein is operably linked to suitable control sequences capable of effecting the expression of a Vitamin K dependent protein in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation.

Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, and integratable DNA fragments (i.e., fragments integratable into the host genome by recombination). The vector replicates and functions independently of the host genome, or may, in some instances, integrate into the genome itself. Expression vectors should contain a promoter and RNA binding sites which are operably linked to the gene to be expressed and are operable in the host organism.

DNA regions are operably linked or operably associated when they are functionally related to each other. For example, a promoter is operably linked to a coding sequence if it controls the transcription of the sequence; or a ribosome binding site is operably linked to a coding sequence if it is positioned so as to permit translation.

Transformed host cells are cells which have been transformed or transfected with one or more Vitamin K dependent protein vector(s) constructed using recombinant DNA techniques.

In a preferred embodiment, a promoter for the elongation factor-1α from Chinese hamster is used (CHEF1) to provide high level expression of a vitamin K dependent coagulation factor and/or processing factor(s). The CHEF1 vector is used as described in Deer, et al. (2004) "High-level expression of proteins in mammalian cells using transcription regulatory sequences from the Chinese Hamster EF-1α gene" Biotechnol. Frog. 20: 880-889 and in U.S. Pat. No. 5,888,809 which is incorporated herein by reference. The CHEF1 vector utilizes the 5' and 3' flanking sequences from the Chinese hamster EF-1α. The CHEF1 promoter sequence includes approximately 3.7 kb DNA extending from a SpeI restriction site to the initiating methionine (ATG) codon of the EF-1α protein. The DNA sequence is set forth in SEQ ID NO: 1 of U.S. Pat. No. 5,888,809.

Host Cells

Suitable host cells include prokaryote, yeast or higher eukaryotic cells such as mammalian cells and insect cells. Cells derived from multicellular organisms are a particularly suitable host for recombinant Vitamin K Dependent protein synthesis, and mammalian cells are particularly preferred. Propagation of such cells in cell culture has become a routine procedure (Tissue Culture, Academic Press, Kruse and Patterson, editors (1973)). Examples of useful host cell lines are VERO and HeLa cells, Chinese hamster ovary (CHO) cell lines and WI138, HEK 293, BHK, COS-7, CV, and MDCK cell lines. Expression vectors for such cells ordinarily include (if necessary) an origin of replication, a promoter located upstream from the DNA encoding vitamin K dependent protein(s) to be expressed and operatively associated therewith, along with a ribosome binding site, an RNA splice site (if intron-containing genomic DNA is used), a polyadenylation site, and a transcriptional termination sequence. In a preferred embodiment, expression is carried out in Chinese Hamster Ovary (CHO) cells using the expression system of U.S. Pat. No. 5,888,809, which is incorporated herein by reference.

The transcriptional and translational control sequences in expression vectors to be used in transforming vertebrate cells are often provided by viral sources. For example, commonly used promoters are derived from Cauliflower mosaic virus (cmv), polyoma, Adenovirus 2, and Simian Virus 40 (SV40). See, e.g., U.S. Pat. No. 4,599,308.

An origin of replication may be provided either by construction of the vector to include an exogenous origin, such as may be derived from SV 40 or other viral (e.g. Polyoma, Adenovirus, VSV, or BPV) source, or may be provided by the host cell chromosomal replication mechanism. If the vector is integrated into the host cell chromosome, the latter is often sufficient.

Rather than using vectors which contain viral origins of replication, one can transform mammalian cells by the method of cotransformation with a selectable marker and the DNA for the Vitamin K Dependent protein(s). Examples of suitable selectable markers are dihydrofolate reductase (DHFR) or thymidine kinase. This method is further described in U.S. Pat. No. 4,399,216 which is incorporated by reference.

Other methods suitable for adaptation to the synthesis of Vitamin K Dependent protein(s) in recombinant vertebrate cell culture include those described in M-J. Gething et al., Nature 293, 620 (1981); N. Mantel et al., Nature 281, 40; A. Levinson et al., EPO Application Nos. 117,060A and 117,058A.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Prokaryote host cells include gram negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the betalactamase (penicillinase) and lactose promoter systems (Chang et al., Nature 275, 615 (1978); and Goeddel et al., Nature 281, 544 (1979)), a tryptophan (trp) promoter system (Goeddel et al., Nucleic Acids Res. 8, 4057 (1980) and EPO App. Publ. No. 36,776) and the tac promoter (H. De Boer et al., Proc. Natl. Acad. Sci. USA 80, 21 (1983)). The promoter and Shine-Dalgarno sequence (for prokaryotic host expression) are operably linked to the DNA encoding the Vitamin K Dependent protein(s), i.e., they are positioned so as to promote transcription of Vitamin K Dependent Protein(s) messenger RNA from the DNA.

Eukaryotic microbes such as yeast cultures may also be transformed with Vitamin K Dependent Protein-encoding vectors see, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding one or more Vitamin K Dependent proteins, sequences for polyadenylation and transcription termination, and a selection gene. An exemplary plasmid is YRp7, (Stinchcomb et al., Nature 282, 39 (1979); Kingsman et al., Gene 7, 141 (1979); Tschemper et al., Gene 10, 157 (1980)). Suitable promoting sequences in yeast vectors include the promoters for metallothionein, 3-phosphoglycerate kinase (Hitzeman et al., J. Biol. Chem. 255, 2073 (1980) or other glycolytic enzymes (Hess et al., J. Adv. Enzyme Reg. 7, 149 (1968); and Holland et al., Biochemistry 17, 4900 (1978)). Suitable vectors and promoters for use in yeast expression are further described in R. Hitzeman et al., EPO Publn. No. 73,657.

Cloned genes of the present invention may code for any species of origin, including mouse, rat, rabbit, cat, porcine, and human, but preferably code for Vitamin K dependent proteins of human origin, DNA encoding Vitamin K dependent proteins that is hybridizable with DNA encoding for proteins disclosed herein is also encompassed. Hybridization of such sequences may be carried out under conditions of reduced stringency or even stringent conditions (e.g., conditions represented by a wash stringency of 0.3M NaCl, 0.03M sodium citrate, 0.1% SDS at 60° C. or even 70° C. to DNA encoding the Vitamin K dependent protein disclosed herein in a standard in situ hybridization assay. See J. Sambrook et al., Molecular Cloning, A Laboratory Manual (2d Ed. 1989) (Cold Spring Harbor Laboratory)).

As noted above, the present invention provides a method of providing a functional Vitamin K dependent proteins. In general, the method comprises culturing a host cell which expresses a vitamin K dependent protein; and then harvesting the proteins from the culture. The culture can be carried out in any suitable fermentation vessel, with a growth media and under conditions appropriate for the expression of the vitamin K dependent protein(s) by the particular host cell chosen. Vitamin K dependent protein can be collected directly from the culture media, or the host cells lysed and the vitamin K dependent protein collected therefrom. Vitamin K dependent protein can then be further purified in accordance with known techniques.

As a general proposition, the purity of the recombinant protein produced according to the present invention will preferably be an appropriate purity known to the skilled art worker to lead to the optimal activity and stability of the protein. The vitamin K dependent protein, such as Factor IX or Factor VII/VIIa is preferably of ultrahigh purity. Preferably, the recombinant protein has been subjected to multiple chromatographic purification steps, such as affinity chromatography, ion-exchange chromatography and preferably immunoaffinity chromatography to remove substances which cause fragmentation, activation and/or degradation of the recombinant protein during manufacture, storage and/or use. Illustrative examples of such substances that are preferably removed by purification include thrombin and Factor IXa; other protein contaminants; proteins, such as hamster proteins, which are released into the tissue culture media from the production cells during recombinant protein production; non-protein contaminants, such as lipids; and mixtures of protein and non-protein contaminants, such as lipoproteins. The purification of the recombinant vitamin K dependent protein may also include in vitro activation of the zymogen into the active protease form. For example, in the case of Factor VII, purification may optionally include an in vitro activation step to Factor VIIa.

Purification procedures for vitamin K dependent proteins are known in the art. For example, see U.S. Pat. No. 5,714,583, which is incorporated herein by reference. A method commonly used in purification of vitamin K dependent protein is pseudochromatography which involves metal ion elution froth a positively charged resin such as Q-Sepharose HP (See U.S. Pat. No. 4,981,952 which is incorporated herein by reference) In the case of vitamin. K dependent proteins, the method relies upon the ability of the gla domain to bind metal ions such as calcium.

Factor IX DNA coding sequences, along with vectors and host cells for the expression thereof, are disclosed in European Patent App. 373012, European Patent App. 251874, PCT Patent Appl. 8505376, PCT Patent Appln. 8505125, European Patent Appln. 162782, and PCT Patent Appln. 8400560. Genes for other coagulation factors are also known and available, for example, Factor II (Accession No. NM_000506), Factor VII (Accession No. NM_019616, and Factor X (Accession No. NM_000504).

It will be understood by those of skill in the art that numerous and various modifications can be Made without departing from the spirit of the present invention. Therefore, it should be clearly understood that the forms of the present invention are illustrative only and are not intended to limit the scope of the present invention.

Pharmaceutical Compositions

The blood clotting Factor formulations may be formed by methods well known in the art. Vitamin K dependent protein compositions may be blended with conventional excipients such as binders, including gelatin, pre-gelatinized starch, and the like; lubricants, such as hydrogenated vegetable oil, stearic acid and the like; diluents, such as lactose, mannose, and sucrose; disintegrants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations which are intended to be converted, shortly before use, to liquid form preparations for either oral or parental administration. Such liquid forms include solutions, suspensions, and emulsions.

These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric measuring device.

Pharmaceutical compositions of Vitamin K dependent protein for injection or intravenous administration comprise therapeutically effective amounts of Vitamin K dependent protein and an appropriate physiologically acceptable carrier. A variety of aqueous carriers may be used, e.g., buffered water, saline, 0.3% glycine and the like. Stabilizers such as plant-derived glycoproteins, albumin, free amino acids, small peptides, lipoprotein, and/or globulin may also be added. Other components of the pharmaceutical compositions of the invention can include pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like, as well as combinations thereof. The liquid utilized will be chosen with regard to the route of administration.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients.

EXAMPLES

Example 1

Determination of Factor IX Antigen Level

A gene for Factor IX was synthesized, operably linked to the CHEF-1 promoter, and, transfected into CHO cells. The primary transfectants were grown up in a 6-well microtiter plate and were assayed in triplicate to give an average level of antigen expression for the cells in the well. As presented in Table 1, the cells were designated primary transfectant line T-335. It should be kept in mind that this is an average production for the primary, transfectants. Some of the cells produce no Factor IX, some produce a moderate level and some cells produce high levels of the protein. The primary transfectants were followed by measuring the amount of Factor IX antigen produced. Biological activity was not measured at this early stage of expression. As a control, a Factor IX gene construct in which the wild type Factor IX Propeptide sequence was replaced with the Propeptide sequence from another Vitamin K dependent protein, Protein C, was transfected into CHO cells and designated primary transfectant cell line T-337.

TABLE 1

Expression of wild type Factor IX in transfected CHO cells.

| Primary Transfectant | Promoter | Factor IX Construct | Replicate (6-well model assay) | | | |
|---|---|---|---|---|---|---|
| | | | A (mg/L) | B (mg/L) | C (mg/L) | AVG (mg/L) |
| T-335 | CHEF-1 | Wild Type Factor IX | 11.8 | 12.0 | 10.7 | 11.5 |
| T-337 | CHEF-1 | Protein C Propeptide - Factor IX | 10.0 | 11.8 | 12.3 | 11.3 |

All transfectants were assayed for Factor IX antigen by a commercially available ELISA test which used a commercially available Factor IX preparation as a standard (BeneFix, Wyeth Laboratories).

The cloning and growth of CHO cells transfected with the Factor IX gene are conducted by one of three methods. As one skilled in the art appreciates, cell cultures are set up to produce the amount of cells or tissue culture fluid needed for the experiments which are performed with these materials. The smallest size system is growth of cells in 96-well microtiter plates. The cells on these plates were grown for 14 days but since they have the smallest surface area for cells to multiply on, they produce the fewest cells and in the least amount of tissue culture media and lowest amounts of Factor IX. The second system is a 6-well model assay as shown in Table 1 above. Cells were grown on a 6 well tissue culture plates for 9 days. Cells grown in 6 well plates generally produce an intermediate amount of cells in a medium amount of tissue culture media and an intermediate amount of Factor IX. The highest concentration (and actual number) of cells was produced in a 1.5 liter shake flask incubated for 18 days.

Due to our extensive experience using all three of systems, it is possible to extrapolate from the amount of Factor IX produced in one system to that produced in another system. For example, the amount of Factor IX produce in the shake Flask system is essentially 6 times greater than produced in the 6-well model system. In this way, when it is necessary for comparison, one can extrapolate the quantity of Factor IX that will be produced in a Shake Flask system from the amount measured in a smaller system like the 6-well model or from the 96-well microtiter plates. Table 1 above indicates that CHO cells can be transfected with a wild type Factor IX gene and produce an average of 11.5 mg/L in a 6-well model assay system. By extrapolation, as described above, this equates to 69 mg/L in a 1.5 L shake flask.

Example 2

For comparison, the wild type Factor IX gene of Example 1 was cloned into a construct using the CMV promoter and transfected into HEK293 cells. As in Example 1 above, the primary transfectants were grown up in a 6-well microliter plate. The titer for these samples was less than 0.2 mg/L (data not shown). Further experiments were conducted using the CHEF-1 promoter.

Example 3

In order to identify and characterize clones with high levels of Factor IX expression, primary transfectants were cloned by limit dilution into 96-well plates. As a consequence of the low surface area for cells to grow the level of expression was less that that reported in Example 1 where cells were grown on 6-well microliter plates. One hundred and fifty two single cell clones were identified from the T-335 primary transfectant experiment. The Factor IX antigen expression level for each clone was measured by ELISA analysis. The distribution of Factor IX expression levels from the clones are shown in FIG. 1.

The T-335 clones were separated into clones that expressed Factor IX at a level of greater than 0.4 mg/L and those that produced Factor IX at lower levels. Clones expressing Factor IX at levels higher than 0.4 mg/L were considered high expresser clones. Clones with expression levels lower than 0.4 mg/L were considered low expressers. The range of expression for Factor IX can be seen to be distributed in a wide range between no expression to above 1.6 mg/L with an average of 0.87 mg/L of Factor IX. In order to determine if other genes transfected into CHO Cells would have essentially the same broad range of distribution when recloned, cells form the primary T-337 transfection were also cloned by limit dilution in the 96-well microtiter plate assay. As can be seen in FIG. 1 above and Table 2 below, of the 171 clones evaluated the range of antigen expression was again quite broad being between none and above 1.8 mg/L with an average of 0.73 mg/L.

TABLE 2

Limit dilution cloning of Primary Transfectants

| Primary Transfectant Cloned | | Factor IX Antigen Level | |
| --- | --- | --- | --- |
| | # of Clones | All Clones mg/L | High Expressors mg/L |
| T335 Wild Type Factor IX | 152 | 0.46 | 0.87 |
| T337 Protein C Propeptide-Factor IX | 171 | 0.29 | 0.73 |

The results of FIG. 1 and Table 2 demonstrate that when CHO cells are transfected with a gene under the control of the CHEF-1 promoter, all cells are not transfected in a way that they can produce detectable Factor IX and that those cells that are transfected in a productive way produce varying amounts of Factor IX. The reason that these cells produce varying levels of Factor IX is not understood. Without intending to be limited by theory, reasons may include that (1) some cells simply do not receive the transfected gene, (2) others may receive a gene copy but it may not integrate into the chromosome, (3) other cells may have the gene integrated in a non-functional region of the chromosome, (4) yet other cells may receive multiple copies of the gene but only some are integrated in the correct position of the genome for expression and (5) some cells may receive multiple copies of the gene but only some of the copies are integrated in a functional way at the time the ELISA is performed on individual clones. The last possibility predicts that as these cells divide and grow, more copies of unintegrated DNA may become integrated with time, (6) Duplication of integrated plasmid may occur and number of duplications may increase upon further cloning or culturing. In the last two cases (5) and (6), one predicts that upon further cloning or culturing, (essentially repeating the above experiment), cell lines would be isolated which would express higher levels of Factor IX (or other protein, e.g., Factor VII/VIIa).

To determine if this were the case, high level expressors of Wild Type Factor IX, as described in Table 2, were pooled and expanded in a shake flask culture. Individual clones were then isolated by limit dilution cloning. The clones producing the highest level of Factor IX were isolated. The twenty highest producers are presented in Table 3.

TABLE 3

Second limit dilution of pooled high expressing clones of T-335 and selection for high Factor IX antigen expression.

| Sample # | Titer (µg/mL) | Clot Time | FIX Activity (U/mL) | Specific Activity (U/mg) | Active FIX (µg/mL) | % Active FIX | Estimated 6-Well Titer (µg/mL) |
| --- | --- | --- | --- | --- | --- | --- | --- |
| P1B10 | 4.14 | 65.95 | 0.066 | 16 | 0.264 | 6% | 104 |
| P2B11 | 3.05 | 76.54 | 0.028 | 9 | 0.112 | 4% | 76 |
| P1G12 | 2.98 | 66.26 | 0.077 | 26 | 0.308 | 10% | 75 |
| P2C2 | 2.47 | 67.11 | 0.062 | 25 | 0.248 | 10% | 62 |
| P1H2 | 2.44 | 61.66 | 0.100 | 41 | 0.400 | 16% | 61 |
| P1A6 | 2.31 | 65.00 | 0.071 | 31 | 0.284 | 12% | 58 |
| P1B4 | 2.16 | 64.65 | 0.074 | 34 | 0.296 | 14% | 54 |
| P1G3 | 2.12 | 65.87 | 0.079 | 37 | 0.316 | 15% | 53 |
| P1A12 | 2.03 | 70.04 | 0.046 | 23 | 0.184 | 9% | 51 |
| P1A2 | 2.02 | 75.28 | 0.030 | 15 | 0.120 | 6% | 50 |
| P1H10 | 1.98 | 65.60 | 0.069 | 35 | 0.276 | 14% | 50 |
| P2D7 | 1.97 | 62.34 | 0.095 | 48 | 0.380 | 19% | 49 |
| P2D6 | 1.95 | 63.41 | 0.086 | 44 | 0.344 | 18% | 49 |
| P1D11 | 1.94 | 66.37 | 0.076 | 39 | 0.304 | 16% | 49 |
| P1D9 | 1.92 | 62.32 | 0.110 | 57 | 0.440 | 23% | 48 |
| P2D11 | 1.85 | 58.42 | 0.138 | 74 | 0.552 | 30% | 46 |
| P1H3 | 1.85 | 66.61 | 0.063 | 34 | 0.252 | 14% | 46 |
| P1G4 | 1.83 | 68.11 | 0.065 | 35 | 0.260 | 14% | 46 |
| P1B5 | 1.83 | 68.66 | 0.052 | 28 | 0.208 | 11% | 46 |
| P1E6 | 1.79 | 69.77 | 0.057 | 32 | 0.228 | 13% | 45 |

The "estimated 6-well titers" is based on our experience that about 25-fold more antigen is produced in 6-well plates when Compared to 96-well plates.

Figure 2:
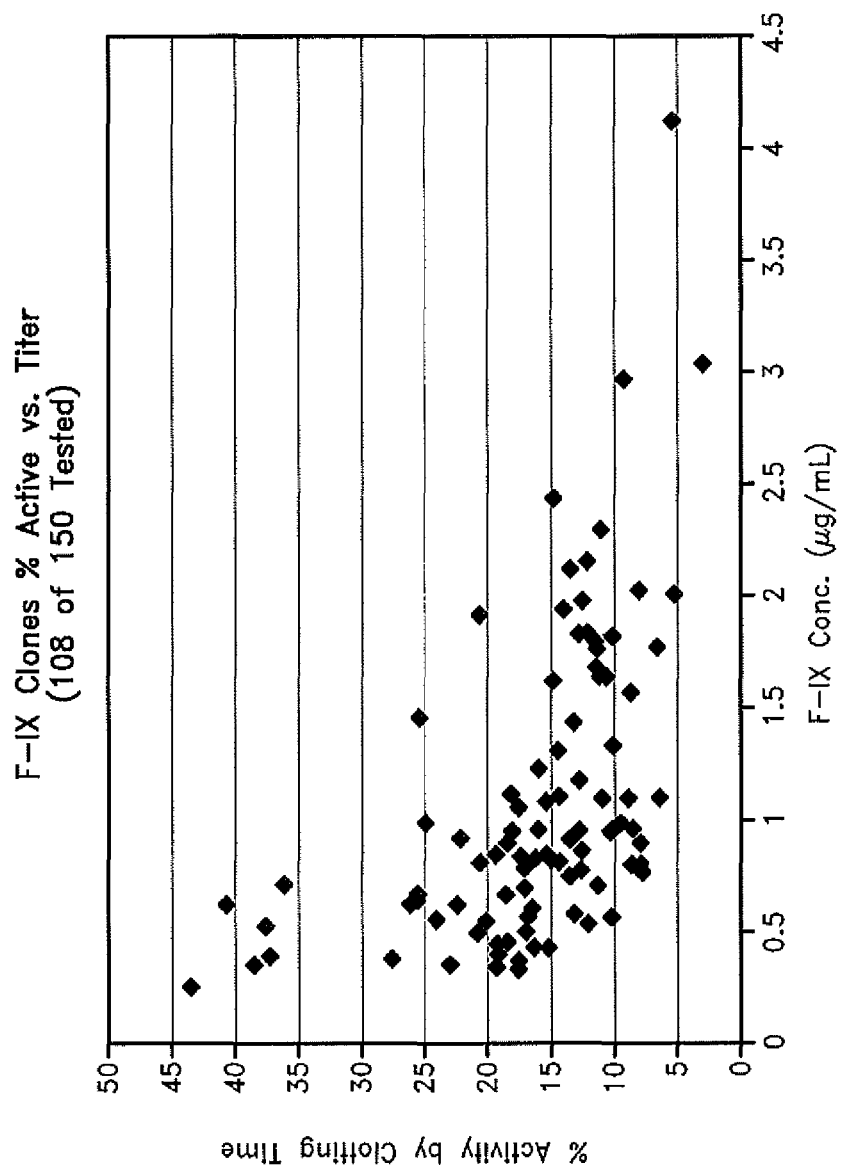
FIG. 2 shows Factor IX clones % activity versus titer.

As shown in Table 3, in the 96 well microliter model, the range of production for Factor IX antigen from the highest yielding 20 clones is between 1.79 and 4.14 mg/L. As presented in the last column of Table 3, one can estimate the concentration of Factor IX that would be expected in 6-well microtiter plates. It is estimated that the level of these clones in 6-microtitre plates would be between 46 and 104 mg/L. This is a substantial increase from the level of expression of the primary transfectants seen in Table 2 (a range of 0-1.65 mg/L was reported). The biological activity of Factor IX produced from this selected group of clones is between 4 and 30% (Table 3). It appears, that, in general, the higher the level of Factor IX antigen production the lower the level of biologically active Factor IX produced. This is shown graphically in FIG. 2. This observation has been made by others attempting to overproduce Vitamin K dependent coagulation factors.

It has always proven difficult to produce Factor IX in tissue culture systems with more than 1.5-5% biologically activity. For example, Kaufman (Kaufman, et al. The Journal of Biological Chemistry vol. 261 (21):9622-9628, Jul. 25, 1986) report CHO cell lines secreting more than 100 µg/ml Factor IX by methotrexate amplification in dihyrofolate reductase deficient cell lines. Yet, biologically active Factor IX was never produced at a level higher than 1.5 µg/ml. It was suggested that the CHO cell line was deficient in processing factors needed to make biologically active Factor IX. It is generally accepted that the presence of processing cofactors is necessary to produce biologically active vitamin K dependent proteins in recombinant systems. We evaluated the potential of our selection system to also identify clones producing a high percentage of biologically active Factor IX. Table 4 presents the 20 Factor IX producing clones with the highest percentage of biologically active Factor IX.

TABLE 4

Second limit dilution of high expresser clones of T-335 and selection for high percentage of biologically active Factor IX.

| Sample # | Titer (µg/mL) | Clot Time | FIX Activity (U/mL) | Specific Activity (U/mg) | Active FIX (µg/mL) | % Active FIX | Estimated 6-Well Titer (µg/mL) |
|---|---|---|---|---|---|---|---|
| P2A7 | 0.24 | 76.52 | 0.028 | 119 | 0.112 | 48% | 6 |
| P1B9 | 0.61 | 65.52 | 0.088 | 112 | 0.272 | 45% | 15 |
| P2D5 | 0.47 | 69.04 | 0.052 | 112 | 0.208 | 45% | 12 |
| P2A10 | 0.34 | 73.28 | 0.036 | 106 | 0.144 | 42% | 8 |
| P2B9 | 0.51 | 68.62 | 0.053 | 103 | 0.212 | 41% | 13 |
| P1B11 | 0.38 | 71.82 | 0.039 | 103 | 0.156 | 41% | 10 |
| P1D10 | 0.70 | 67.28 | 0.070 | 99 | 0.280 | 40% | 18 |
| P2D2 | 0.88 | 63.63 | 0.085 | 96 | 0.340 | 39% | 22 |
| P2C5 | 0.37 | 74.30 | 0.034 | 92 | 0.136 | 37% | 9 |
| P2D3 | 0.67 | 68.06 | 0.057 | 86 | 0.228 | 34% | 17 |
| P2A9 | 0.37 | 76.33 | 0.028 | 76 | 0.112 | 30% | 9 |
| P2D11 | 1.85 | 58.42 | 0.138 | 74 | 0.552 | 30% | 46 |
| P1H11 | 0.61 | 70.83 | 0.044 | 72 | 0.176 | 29% | 15 |
| P1E8 | 0.65 | 72.25 | 0.046 | 71 | 0.184 | 28% | 16 |
| P1E9 | 0.64 | 72.55 | 0.045 | 70 | 0.180 | 28% | 16 |
| P1E3 | 1.45 | 63.08 | 0.102 | 70 | 0.408 | 28% | 36 |
| P1E10 | 0.98 | 67.76 | 0.067 | 69 | 0.268 | 27% | 24 |
| P2E8 | 0.30 | 81.39 | 0.020 | 67 | 0.080 | 27% | 7 |
| P1C9 | 0.54 | 72.96 | 0.036 | 66 | 0.144 | 27% | 14 |
| P2D10 | 0.79 | 69.59 | 0.050 | 64 | 0.200 | 25% | 20 |

As can be seen in Table 4, all of the 20 clones producing Factor IX, which have been selected for high content of biologically active material produce above 25% biologically active Factor IX. In this experiment, the highest level of functional Factor IX reported is for clone P2A7 at 48%. Specific activity ranges from 64-119 U/mg. In contrast, Kaufman (ibid) reported specific activity of 35-75 U/mg, up to half the specific activity of plasma derived Factor IX (150 U/mg) using the adenovirus major late promoter. By use of the CHEF-1 promoter in $C_{1-10}$ cells, biologically active recombinant Factor IX was produced at levels much closer to the levels obtained with plasma-derived Factor IX. It was unexpected that such high levels of biologically active Factor IX protein could be produced recombinantly without addition of processing factors.

In summary, limit dilution selection of clones which produce Factor IX in a tissue culture system in conjunction with a high level promoter system produced more Factor IX antigen and a higher level of biologically active Factor IX protein than has been possible in the past.

Example 4

In order to determine if our extrapolation of Factor IX production from 96-well plates to 6-well microtiter plates was accurate in both antigen produced and percentage biologically active protein recovered, we expanded a group of eleven clones from the second limited dilution experiment in 6 well microtiter plates. As can be seen in Table 5, the results were similar than those reported in 96 well micro titer plates. The level of Factor IX antigen production was between 2 and 40 mg/L and the percentage of biologically active Factor IX recovered was between 10 and 58%. The level of biologically active Factor IX was significantly higher than reported previously for any other Vitamin K dependent protein prepared in the absence of vitamin K or processing factors involved in post-translational processing of blood factor proteins.

TABLE 5

Factor IX antigen production and percentage of biologically active Factor IX in 6-well microtiter plates.

| Sample # | Titer (mg/L) | Factor IX Activity (U/mL) | Specific Activity (U/mg) | Active FIX (mg/L) | % Active FIX |
|---|---|---|---|---|---|
| 117 | 37.1 | 2.7 | 74 | 11.0 | 30 |
| 143 | 40.1 | 2.2 | 56 | 9.0 | 22 |
| 23 | 16.3 | 1.6 | 101 | 6.6 | 40 |
| 125 | 10.3 | 1.5 | 142 | 5.9 | 57 |
| 46 | 10.3 | 1.5 | 145 | 5.9 | 58 |
| 21 | 10.4 | 1.3 | 121 | 5.1 | 49 |
| 137 | 9.9 | 1.1 | 116 | 4.6 | 46 |
| 106 | 9.2 | 1.1 | 124 | 4.6 | 50 |
| 135 | 7.8 | 0.5 | 66 | 2.1 | 27 |
| 105 | 18.4 | 0.4 | 24 | 1.8 | 10 |
| 103 | 2.7 | 0.3 | 104 | 1.1 | 42 |

As shown by Table 5, extrapolating production and Factor IX antigen and percentage of biologically active Factor IX produced from 96-well microtiter plates to production in 6 well-microtiter plates is confirmed by experimental data.

Example 5

Recombinant Factor VII Produced by Semi-Solid Matrix Cloning

A gene for Factor VII was synthesized, operably linked to the CHEF-1 promoter, and transfected into CHO cells using a vector which included the DHFR marker for selection in Hypoxanthine Thymidine (HT)-minus medium. The primary transfectants were grown up in a microtiter plate and were assayed to give an average level of antigen expression for the cells in the well. The pool of primary transfectants were then subjected to cell cloning by a semi-solid matrix cloning method.

The cells were seeded into a semi-solid matrix at very low densities (typically 1,000-4,000 cells per ml) into a mixture of media (Cloning medium A®, Invitrogen), media supplements (4 mM L-glutamine, 10 ng/1 mL vitamin K, 1 mM $CaCl_2$), conditioned medium (5-20% of 7 day old culture of parental CHO cells), and a generally inert, biologically compatible, semi-solid medium such as methylcellulose (CloneMatrix®). After seeding the low density cells into the mixture as a single cell suspension and letting it "gel" for a few minutes, into a semi-solid, the culture plates are returned to an incubator (37° C., with humidity and carbon dioxide buffering atmosphere) and allowed to sit undisturbed for anywhere from ~1 week to ~3 weeks.

A fluorescent antibody against human FVII was included in the semi-solid medium formulation such that the FVII-antibody that was impregnated in the gel allowed detection of high expressing colonies (clones) when the culture plates containing semi-solid matrix with colonies were viewed under a fluorescence microscope. About two weeks after initially seeding the cells into the semisolid matrix the culture plates were observed for colony formation (number of colonies, their size and how far separated they are from one another in the gel) and then individual colonies were picked and seeded into separate cluster plates, each as a clonal population. They were expanded through larger plates and screened for production of FVII in expansion medium (OptiCHO®, L-glutamine, 200 mM, Vitamin K1 (2% in ethanol) and 1 M $CaCl_2$). The cells were split and grown in fresh medium. Periodically, FVII/FVIIa levels and bioactivity were assessed.

FVII/FVIIa levels were determined by conventional FVII ELISA assay.

Bioactivity was determined by a conventional chromogenic FVIIa Bioactivity assay such as BIOPHEN FVII® (Ref No. 221304) available from HYPHEN BioMed. The basis of the assay relies upon the ability of Factor VII to activate Factor X to Factor Xa. After forming an enzymatic complex with Tissue Factor, provided by rabbit Thromboplastin, the FVII complex activates Factor X to Factor Xa which activity is measured by cleavage of a chromogenic substrate (SXa-11). Factor Xa cleaves the substrate and generates pNA. The amount of pNA generated is directly proportional to the Factor Xa activity. Finally, there is a direct relationship between the amount of Factor VII in the assayed sample and the Factor Xa activity generated, measured by the amount of pNA released, determined by color development at 405 nm. Alternatively, a two-stage coagulation (clotting) assay may be used to determine FVII/FVIIa activity.

Calibration is performed with a normal pooled citrated plasma, with the assigned value of 100% Factor VII. The assay kit includes a standard plasma dilution of 1:1000. By definition, this latter dilution of the pool represents the 100% Factor VII activity. The dynamic range is from 0 to 200% Factor VII. The 200% Factor VII activity is the 1:500 dilution of the plasma pool. A standard curve was generated.

Samples were diluted in order to get a final Factor VII concentration in the tested dilution range of 0.1 to 1 ng/ml. The samples were placed in a microplate well or Plastic tube and incubated. The SXa-11 substrate was introduced followed by further incubation. The reaction, was stopped by adding 60 µL/well or 200 µL/tube citric acid (20 g/L), or 20% acetic acid. The yellow color is stable for 2 hours. The sample blank was prepared by mixing the reagents in the opposite order from the test (i.e., Citric Acid (20 g/L), SXa-11 substrate, diluted plasma, Factor X, and Thromboplastin-Ca). The concentration of bioactive FVII/FVIIa was determined for the unknown samples from the standard curve generated with plasma samples from the kit discussed above. The concentration of bioactive FVII represents the amount in µg/ml of FVII/FVIIa in the supernatant that was sufficiently carboxylated to be measured as "active FVIIa".

Table 6 shows the titers of FVII/VIIa antigen in the supernatants of 15 different clones transfected with a FVII encoding plasmid containing the DHFR selectable marker and a CHEF-1 promoter and how much of this FVII/VIIa protein in the supernatants was biologically active as measured by the chromogenic assay described above. The various clones produce reasonably high levels of FVII/VIIa antigen into their supernatant (e.g. up to 7 ug/ml) even though they do not contain plasmid for expressing any exogenous (human) VKOR or VKGC. More importantly, for these representative clones the proportion of FVII/VIIa antigen in the supernatant which is bioactive is very high, ranging from 66% to 100% of the secreted FVII.

TABLE 6

Titers of FVII/FVIIa antigen and Bioactivity in supernatants of 15 different clones.

| Clone # | Ag (ng/ml) | Bioactivity (ng/ml) | % Bioactive |
| --- | --- | --- | --- |
| 1 | 7152 | 6848 | 96 |
| 2 | 5524 | 5214 | 94 |
| 3 | 5160 | 4194 | 81 |
| 4 | 5042 | 4766 | 95 |
| 5 | 4017 | 3109 | 77 |
| 6 | 4013 | 3009 | 75 |
| 7 | 3924 | 2587 | 66 |
| 8 | 3651 | 3062 | 84 |
| 9 | 3531 | 3937 | 100* |
| 10 | 3377 | 3289 | 97 |
| 11 | 3286 | 2836 | 86 |
| 12 | 3064 | 3520 | 100* |
| 13 | 2891 | 2488 | 86 |
| 14 | 2642 | 2514 | 95 |
| 15 | 2307 | 2341 | 100* |

*calculated value was greater than 100%

Table 7 shows similar kind of data as Table 6 except that these results were obtained from the clones at a later stage, after the individual clones had undergone more cumulative population doublings. The clones have increased their volumetric productivities (i.e. amount of FVII/VIIa antigen per unit volume of culture supernatant) the longer they've been cultured. By comparing the results in Table 7 for Clone #10 with that in Table 6, one sees that this clone's expression levels increased from ~3.3 ug/ml in the secondary screening stage to ~29 ug/ml after time in culture. The secondary screen results are from static cultures grown in cluster plates whereas the later assays are derived from cultures grown under more optimal culture conditions, i.e., in a shaking flask where the cultures are better aerated and with better availability of nutrients before the supernatant sample was harvested for assaying.

TABLE 7

Titers of FVII/FVIIa antigen and Bioactivity in supernatants of 5 selected clones after repeated culturing.

| Clone # | Ag (ng/ml) | Bioactivity (ng/ml) | % Bioactive |
| --- | --- | --- | --- |
| 1 | 23000 | 15000 | 65 |
| 2 | 26000 | 19000 | 73 |
| 3 | 28000 | 20000 | 71 |
| 6 | 26000 | 18000 | 69 |
| 10 | 29000 | 21000 | 72 |

This increase in cell specific productivity (Qp) is shown in the following Table for a particular clone. An increase of 0.4 pg/cell/day at initial assessment increases to 0.56 pg/cell/day as a function of time in culture, without recourse to supertransfection with processing factors. Typical values for FVII/VIIa production before initiation of the cell stability studies was 11-12 µg/mL with 60-70% bioactivity. By the end of productivity assessment #3, these numbers typically increased to 35-45 µg/mL with somewhat higher bioactivity (65-70%).

TABLE 8

Increase in cell specific productivity (Qp) as a function of time in culture

| Experiment | Qp (pg/cell/day) |
| --- | --- |
| Cell Stability flasks: | |
| Prod. Assess #1 | 0.4 (23)* |
| Prod Assess #2 | 0.4 (48) |
| Prod Assess #3 | 0.56 (73) |

*Numbers in parentheses refers to number of total cumulative population doublings from the time the cells recovered from transfection and selection until seeding in the productivity assessment experiment indicated.

These results show that by cell cloning methods such as limit dilution cloning and semi-solid matrix cloning, and with repeated culturing, high levels of bioactive vitamin K dependent proteins can be achieved without co-transfection of processing factors such as VKOR, VKGC, and/or PACE.

It will be understood by those of skill in the art that numerous and various modifications can be made without departing from the spirit of the present invention. Therefore, it should be clearly understood that the forms of the present invention are illustrative only and are not intended to limit the scope of the present invention.

The invention claimed is:

1. A method of producing a vitamin K dependent protein, the method comprising the steps of: (a) transfecting a population of mammalian cells with a gene encoding the vitamin K dependent protein operably linked to a promoter, wherein the mammalian cells do not contain heterologous genetic material encoding proteins involved in the post-translation modification of the vitamin K dependent protein; (b) performing at least one round of cloning and screening to identify cells which produce at least 30 mg/L of the vitamin K dependent protein, wherein at least 10% of the vitamin K dependent protein is biologically active; (c) optionally, repeating step (b) one or more times; and (d) harvesting the vitamin K dependent protein.

2. The method of claim 1, wherein the vitamin K dependent protein is selected from the group consisting of Factor II, Factor VII, Factor IX, Factor X, Protein C and Protein S.

3. The method of claim 2, wherein the vitamin K dependent protein is Factor IX or Factor VII.

4. The method of claim 1, wherein in step (b) the cloning is limit dilution cloning or semi-solid matrix cloning.

5. The method of claim 1, wherein the promoter is a Chinese hamster elongation factor 1 (CHEF-1) promoter.

6. The method of claim 1, further comprising the step of preselecting cells producing at least 10 mg/L vitamin K dependent protein before step (b).

7. The method of claim 1, wherein the cells are cultured in a media that includes vitamin K.

8. The method of claim 1, wherein the cells are cultured in a media that does not include vitamin K.

9. The method of claim 1, wherein in step (b) at least 20% of the vitamin K dependent protein is biologically active.

10. The method of claim 9, wherein at least 30% of the vitamin K dependent protein is biologically active.

11. The method of claim 10, wherein at least 40% of the vitamin K dependent protein is biologically active.

12. The method of claim 1, wherein the mammalian cells are Chinese hamster ovary cells.

13. A method of producing a vitamin K dependent protein, the method comprising the steps of: (a) transfecting a population of mammalian cells with a gene encoding the vitamin K dependent protein operably linked to a Chinese hamster elongation factor 1 (CHEF-1) promoter, wherein the mammalian cells do not contain heterologous genetic material encoding proteins involved in the post-translation modification of the vitamin K dependent protein; and (b) performing at least one round of cloning and screening to identify cells which produce at least 30 mg/L of the vitamin K dependent protein, wherein at least 10% of the vitamin K dependent protein is biologically active.

14. The method of claim 13, wherein the cloning is limit dilution cloning or semi-solid-matrix cloning.

* * * * *